US010149857B2

(12) United States Patent
Smith et al.

(10) Patent No.: US 10,149,857 B2
(45) Date of Patent: Dec. 11, 2018

(54) LYOPHILIZED CYCLOPHOSPHAMIDE COMPOSITION AND METHODS OF PREPARATION THEREOF

(71) Applicant: AMPAC Fine Chemicals LLC, Rancho Cordova, CA (US)

(72) Inventors: Andrew M. Smith, Philadelphia, PA (US); Timothy S. Dutill, Plymouth Meeting, PA (US); Edward H. Trappler, Langhorne, PA (US)

(73) Assignee: AMPAC Fine Chemicals LLC, Rancho Cordova, CA (US)

( * ) Notice: Subject to any disclaimer, the term of this patent is extended or adjusted under 35 U.S.C. 154(b) by 0 days.

(21) Appl. No.: 15/454,420

(22) Filed: Mar. 9, 2017

(65) Prior Publication Data
US 2018/0256608 A1  Sep. 13, 2018

(51) Int. Cl.
*A61K 31/661* (2006.01)
*A61K 47/26* (2006.01)

(52) U.S. Cl.
CPC ......... *A61K 31/661* (2013.01); *A61K 47/26* (2013.01)

(58) Field of Classification Search
CPC ..... C07F 9/6533; C07B 2200/13; A61K 9/19; A61K 9/41; A61K 31/661; A61K 47/26
See application file for complete search history.

(56) References Cited

U.S. PATENT DOCUMENTS

| | | | |
|---|---|---|---|
| 4,537,883 A | 8/1985 | Alexander et al. | |
| 4,659,699 A | 4/1987 | Francis | |
| 4,797,388 A | 1/1989 | Francis | |
| 5,036,060 A | 7/1991 | Alam et al. | |
| 5,227,374 A | 7/1993 | Alexander et al. | |
| 5,413,995 A | 5/1995 | Alexander et al. | |
| 5,418,223 A | 5/1995 | Palepu et al. | |
| 5,972,912 A | 10/1999 | Marek et al. | |
| 6,284,277 B1 | 9/2001 | Bouloumie et al. | |
| 9,023,834 B2 | 5/2015 | Yen et al. | |
| 2015/0218071 A1* | 8/2015 | Boit | C07C 29/78 568/868 |
| 2015/0290226 A1 | 10/2015 | Chandrashekhar et al. | |
| 2015/0314004 A1 | 11/2015 | Li | |

FOREIGN PATENT DOCUMENTS

| | | |
|---|---|---|
| EP | 3 858 325 A1 | 8/1998 |
| EP | 2 985 038 A1 | 2/2016 |
| WO | 9717064 A1 | 5/1997 |
| WO | 2014/068585 A1 | 5/2014 |
| WO | 2016/005962 A2 | 1/2016 |

OTHER PUBLICATIONS

Karle et. al., JACS, 1977, ACS, vol. 99, pp. 4803-4807 (Year: 1977).*
Jones et al, "The Anhydrous Racemate of the Carcinostatic Agent Cyclophosphamide and the Bicyclic Degradation Product 1-(2-Chloroethyl)tetrahydro-1H,5H-1,3,2-diazaphospholo[2,1-b][1,3,2]oxazaphosphorine 9-Oxide," Acta Cryst., C52, pp. 2359-2363 (1996) (Abstract Only).
Adamiak et al, "X-ray-diffraction study and determination of absolute configuration of the anticancer drug S(-) cyclophosphamide (Endoxan, Cytoxan, NSC-26271)," J. BioScience, vol. 32,No. 9-10, pp. 672-677 (1977) (Abstract Only).
Karle et al, "Absolute Configuration of (+)-Cyclophosphamide, a Crystal and Molecular Structure Determination by X-Ray Diffraction," Journal of American Chemical Society, vol. 99, pp. 4803-4807 (1977) (Abstract Only).
Botez et al, "Crystal Structure of Anhydrous d-D-Mannitol," Powder Diffraction, vol. 18, Issue 3, pp. 214-218 (2003) (Abstract Only).
Kim et al, "The Crystal Structure of the K Form of D-Mannitol," Acta Cryst, B24, pp. 1449-1455 (1968) (Abstract Only).
Nunes et al, "Characterization and Crystal Structure of D-Mannitol Hemihydrate," J. Pharm. Sci., vol. 93, pp. 2800-2809 (2004) (Abstract Only).
Kaminsky et al, "Crystal optics of D-mannitol, C6H1406: crystal growth, structure, basic physical properties, birefringence, optical activity, Faraday effect, electro-optic effects and model calculations," Crystalline Materials, vol. 212, pp. 283-296 (1997) (Abstract Only).
Clardy et al, "Crystal and Molecular Structure of the Carcinostat Cyclophosphamide Hydrate," Phosphorus, vol. 4, pp. 151-156 (1974).
Office Action dated Jul. 10, 2018 in U.S. Appl. No. 15/813,736, by Smith.
Semicore Equipment Inc., The Global Source: Semicore, 2018, Pressure conversion chart (2018), downloaded from web page: http://www.linkedin.com/company/semequipment-inc/, download date: Jul. 2018, 9 pages.

* cited by examiner

*Primary Examiner* — Sarah Pihonak
(74) *Attorney, Agent, or Firm* — Panitch Schwarze Belisario & Nadel LLP

(57) ABSTRACT

An improved lyophilized cyclophosphamide solid composition is described. The lyophilized cyclophosphamide solid composition is thermally stable, contains anhydrous cyclophosphamide and mannitol, and is substantially free of cyclophosphamide monohydrate. A method for preparing the lyophilized cyclophosphamide solid composition is also provided.

9 Claims, 2 Drawing Sheets

LYOPHILIZED CYCLOPHOSPHAMIDE COMPOSITION AND METHODS OF PREPARATION THEREOF

BACKGROUND OF THE INVENTION

Cyclophosphamide is a synthetic antineoplastic drug which is chemically related to the nitrogen mustards. Cyclophosphamide, having the chemical name 2-[bis(2-chloroethyl)amino]tetrahydro-2H-1,3,2-oxazaphosphorine 2-oxide, can exist in both monohydrate and anhydrous forms as shown in Formula I and Formula II below:

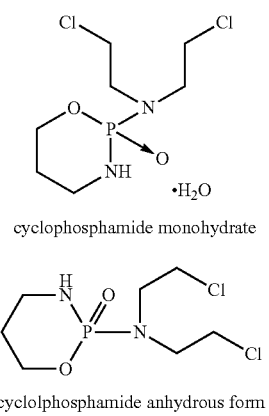

cyclophosphamide monohydrate cyclolphosphamide anhydrous form

The monohydrate form is preferred for pharmaceutical processing, as the anhydrous form was reported to be highly unstable and readily picks up water to form the monohydrate when exposed to a relative humidity of about 20-30% or higher at about 25° C. The monohydrate drug form is stable but, under dry conditions (relative humidity of about 20% or less), begins to lose the water of hydration, giving rise to unwanted degradation products which may potentially impact product quality and end-use limitation. Accordingly, maintaining proper manufacturing and storage conditions are essential to product quality attributes and critical for application for approved regulatory usage.

Cyclophosphamide is available in sterile parenteral dosage formulations consisting of sterile packaged dry powder blend admixtures of cyclophosphamide monohydrate and sodium chloride, which are dissolved in water prior to administration. However, such formulations have disadvantages, such as glassiness and/or stickiness acquired by the powder premix composition during the processing and storage, which might impact overall product quality and end-use applicability, including inferior solubility and decreased potency, as well as deterioration during storage.

Lyophilization, or freeze drying, is a process for creating or isolating a stable preparation of a solid product by freezing and dehydration and/or removal of solvents utilized for dissolution of the frozen product under vacuum. The sublimation of the ice from the frozen solution leaves the solid, dried components of the original liquid.

U.S. Pat. No. 4,537,883 to Alexander et al. discloses that a lyophilized cyclophosphamide solid composition containing 4% moisture gave a product with superior thermal stability, compared to lyophilized cyclophosphamide solid compositions with moisture levels of 1% or less, or even cyclophosphamide itself. It describes two methods to prepare the solid compositions. One method involves lyophilization of a sterile solution of cyclophosphamide, mannitol and water in a short period of time (24 hours) to produce a "dry" lyophilizate having a moisture content of 2% or less, then humidifying the "dry" lyophilizate to give a "hydrated" lyophilizate containing approximately 4% moisture. The other method involves lyophilization of the sterile solution using a longer 2 stage lyophilization process (48 hours), where the first stage of freeze-drying was done with a low condenser temperature of −60° C. and a shelf temperature at 10° C., and when the product temperature (measured by thermocouple) reached about −12° C., the second stage of freeze-drying was conducted by raising the condenser temperature to −30° C. and lowering the shelf temperature to −10° C.

U.S. Pat. No. 4,659,699 to Daniel et al. discloses a two-stage process involving freeze drying an aqueous solution of cyclophosphamide with an excipient until the moisture content is less than 2% by weight, then rehydrating the freeze dried material to the moisture content in the critical range of 2-7% by weight.

U. S. Patent Application Publication No. 2015/0290226 of Chandrashekhar et al. describes a lyophilization process that did not need rehydration step and produced crystalline monohydrate form containing 5.7 to 6.8% of water. The lyophilization was conducted with one or more organic solvents or a mixture of organic solvent(s) and water.

Many known lyophilized preparations of cyclophosphamides or similar drugs contain components such as bulking or matrix forming agents. These additives include salts such as sodium chloride, mono-, di- and polysaccharides, and sugar alcohols such as mannitol. D-mannitol is known to exist as three polymorphs: α (also known as κ), β, and δ. Preparations which are mannitol free are also known. For example, U.S. Pat. No. 5,036,060 of Alam et al. describes a mannitol-free lyophilized formulation of cyclophosphamide. The formulation is prepared from a solution of cyclophosphamide, water, and sodium chloride, and involves performing several freezing and cooling steps, applying vacuum, and drying until a target moisture content is achieved.

Many prior art processes require a rehydration step at the end of processing, and others require the use of solvents other than water. These processes are disadvantageous for several reasons. For examples, a rehydration step may result in significant variability in the moisture level from vial to vial within a single batch, as well as variability from batch to batch. The use of solvents other than water introduces additional residual materials that must be quantified and controlled.

There is a need for improved lyophilized cyclophosphamide compositions and improved methods for lyophilizing cyclophosphamide.

BRIEF SUMMARY OF THE INVENTION

It was unexpectedly discovered in the present invention that an improved lyophilized cyclophosphamide solid composition containing anhydrous cyclophosphamide and mannitol is thermally stable over extended storage periods, even when the composition has a moisture content less than 1% by weight. The solid composition contains one or more crystalline forms that cannot be attributed to any of the known forms of cyclophosphamide or mannitol.

The solid cyclophosphamide composition can be obtained by an improved lyophilization process that does not require a rehydration step or an organic solvent. Different from the two stage lyophilization process described in U.S. Pat. No.

4,537,883, the present lyophilization process does not require measuring the temperature of the product during freeze-drying, nor a second stage freeze drying at a condenser temperature of −30° C. and a shelf temperature of −10° C. Moreover, the lyophilized composition obtained from the present lyophilization process contains a moisture level much less than 4% by weight as that obtained from the lyophilization process of U.S. Pat. No. 4,537,883.

Accordingly, in one general aspect, the invention relates to a lyophilized cyclophosphamide solid composition comprising cyclophosphamide and mannitol, wherein the composition contains one or more crystalline forms exhibiting an X-ray powder diffraction (XRPD) spectrum having one or more peaks at diffraction angle (2θ) of 8.1±0.2°, 8.5±0.2°, 12.3±0.2° or 13.4±0.2°, preferably a peak at 2θ of 8.5±0.2°. In one embodiment of the invention, the lyophilized cyclophosphamide solid composition contains one or more crystalline forms exhibiting an XRPD spectrum having the peaks at diffraction angle (2θ) of 8.1±0.2°, 8.5±0.2°, 12.3±0.2° and 13.4±0.2°. The assignments for these characteristic peaks are determined by reference XRPD diffractograms.

In one embodiment of the invention, the lyophilized cyclophosphamide solid composition has a moisture content of less than 2% by weight, preferably less than 1% by weight. Preferably, the composition consists essentially of anhydrous cyclophosphamide and mannitol. More preferably, the lyophilized cyclophosphamide solid composition is substantially free of cyclophosphamide monohydrate.

In another embodiment of the invention, the lyophilized cyclophosphamide solid composition has a weight ratio of cyclophoshamide anhydrous to mannitol within a range of about 0.05 to 10, more preferably about 0.05 to 5, even more preferably about 1.2 to 1.8, most preferably about 1.3 (1 part mannitol to 1.33 parts anhydrous cyclophosphamide).

In a preferred embodiment of the invention, the lyophilized cyclophosphamide solid composition consists essentially of cyclophosphamide and mannitol, wherein the composition contains one or more crystalline forms having an X-ray powder diffraction (XRPD) spectrum comprising a peak at 2θ of 8.5±0.2°, preferably peaks at 2θ of 8.5±0.2°, 8.1±0.2°, 12.3±0.2° and 13.4±0.2°. The cyclophosphamide can be predominantly or only present in the anhydrous form.

In another general aspect, the invention relates to a process for producing a lyophilized cyclophosphamide solid composition. The process does not involve a rehydration step, and comprises:

(1) preparing a solution containing cyclophosphamide, mannitol, and water;
(2) filling a receptacle with the solution;
(3) inserting the receptacle filled with the solution into a lyophilizer having a first shelf temperature of 0° C. to 25° C., and maintaining the first shelf temperature to allow all the solution to equilibrate at the first shelf temperature;
(4) cooling the lyophilizer to a second shelf temperature of −75° C. to −30° C. at a first controlled rate, and maintaining the second shelf temperature to allow the solution to form ice and to allow the temperature of the ice to reach a steady state;
(5) chilling the condenser of the lyophilizer to a temperature below −40° C., preferably −50° C. or below;
(6) evacuating the chamber of the lyophilizer to a pressure of less than 4500 μm Hg;
(7) warming the lyophilizer to a third shelf temperature of −30° C. to 40° C. at a second controlled rate, and maintaining the third shelf temperature and the chamber pressure at the pressure of less than 4500 μm Hg to allow sublimation of the ice and thereby produce a sublimed composition; and
(8) setting the lyophilizer to a fourth shelf temperature of 0° C. to 40° C., and maintaining the fourth shelf temperature and the chamber pressure at the pressure of less than 4500 μm Hg to desorb remaining moisture and thereby produce the lyophilized cyclophosphamide solid composition.

In one embodiment of the invention, a solution containing cyclophosphamide, mannitol and water, is prepared by a method comprising:

(a) adding mannitol to water to obtain a mannitol solution;
(b) chilling the mannitol solution to 0° C. to 20° C.; and
(c) admixing cyclophosphamide monohydrate to the mannitol solution at 0° C. to 20° C. to obtain the solution containing cyclophosphamide, mannitol, and water.

In one embodiment of the invention, the cyclophosphamide monohydrate used for the preparation of the lyophilization solution has a particle size that facilitates the efficient dissolution of cyclophosphamide monohydrate, preferably, the cyclophosphamide monohydrate has a d(0.5) particle size distribution of 300 μm to 800 μm, more preferably 100 to 400 μm.

In another embodiment of the invention, the lyophilization solution contains 5 to 25 mg/mL cyclophosphamide monohydrate and 5 to 25 mg/mL mannitol Preferably, the solution containing cyclophosphamide, mannitol and water is sterilized, for example, by filter sterilization. More preferably, the lyophilization solution is prepared, sterilized, filled in the receptacle, and placed in the lyophilizer under conditions without significant degradation of cyclophosphamide.

According to embodiments of the invention, the lyophilizer is precooled to a first shelf temperature before the cyclophosphamide solution is loaded. Preferably, the first shelf temperature is 0° C. to 25° C., such as 0, 1, 2, 3, 4, 5, 6, 7, 8, 9, 10, 11, 12, 13, 14, 15, 16, 17, 18, 19, 20, 21, 22, 23, 24, or 25° C. After the cyclophosphamide solution is loaded to the lyophilizer, the first shelf temperature is maintained, for example, for 1 to 15 hours, such as 1, 2, 3, 4, 5, 6, 7, 8, 9, 10, 11, 12, 13, 14, or 15 hours or any time periods in between, to allow all the solution to equilibrate at the first shelf temperature.

The lyophilizer is then chilled to a second shelf temperature of −75° C. to −30° C., such as −75, −74, −73, −72, −71, −70, −69, −68, −67, −66, −65, −64, −63, −62, −61, −60, −59, −58, −57, −56, −55, −54, −53, −52, −51, −50, −49, −48, −47, −46, −45, −44, −43, −42, −41, −40, −39, −38, −37, −36, −35, −34, −33, −32, −31, or −30° C., at a controlled rate, such as 6 to 120° C. per hours, more preferably at, but not limited to, 25° C., 30° C. or 35° C. per hour. The second shelf temperature is maintained for a period of time sufficient to allow the solution to form ice and to allow the temperature of the ice to reach a steady state prior to proceeding to evacuation. For example, the second shelf temperature can be maintained for 1-20 hours, such as 1, 2, 3, 4, 5, 6, 7, 8, 9, 10, 11, 12, 13, 14, 15, 16, 17, 18, 19, or 20 hours or any time periods in between.

The condenser of the lyophilizer is chilled to a temperature below −40° C., preferably −50° C. or below, such as −45, −50, −55, −60° C., or even lower. The chamber of the lyophilizer is evacuated to a pressure of less than about 4500 μm Hg, such as pressures of 150 to 250 μm Hg. The pressure is maintained by, for example, but not limited to, bleeding in nitrogen gas that is filtered through a 0.1 or 0.2 μm filter.

For the primary drying, the lyophilizer is warmed to a third shelf temperature at a second controlled rate. The third shelf temperature is selected to drive sublimation while maintaining the product temperatures in a safe range to prevent a change upon completion of sublimation. The controlled rate is selected to prevent breakage of the container (e.g., vials) during the ramp. Preferably, the third shelf temperature is −30° C. to 40° C., such as −30, −29, −28, . . . 39, or 40° C., more preferably 5 to 15° C., and the second controlled rate is 6° C. to 120° C. per hour, such as, but not limited to, 10° C., 15° C. or 20° C. per hour. The chamber pressure is maintained under vacuum (e.g., at the pressure of less than about 4500 μm Hg) for a period of time sufficient for all the product temperatures to raise and reach a steady state at or near the third shelf temperature, e.g., to allow sublimation of the ice to thereby produce a sublimed composition. For example, the chamber pressure can be maintained under vacuum for 10-360 hours.

The sublimed composition is further dried at a fourth shelf temperature of 0° C. to 40° C., such as 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40° C., under vacuum. This additional drying step desorbs remaining moisture to thereby produce a lyophilized cyclophosphamide solid composition of the invention. The additional drying step can be conducted for, e.g., 3 to 12 hours, or a longer period of time as needed.

The lyophilization process is stopped by raising the pressure of the chamber of the lyophilizer, for example, to about 1 to about 14.7 psia, more preferably about 10.0 psia, and stoppering the receptacle containing the lyophilized cyclophosphamide solid composition.

Another aspect of the present invention relates to a lyophilized cyclophosphamide preparation that is prepared by a method of the invention.

BRIEF DESCRIPTION OF THE SEVERAL VIEWS OF THE DRAWINGS

The foregoing summary, as well as the following detailed description of the invention, will be better understood when read in conjunction with the appended drawings. These drawings are included for the purpose of illustrating a preferred embodiment of the invention. The invention is not limited to the precise arrangements and instrumentalities shown.

In the drawings.

DETAILED DESCRIPTION OF THE INVENTION

Figure 1:
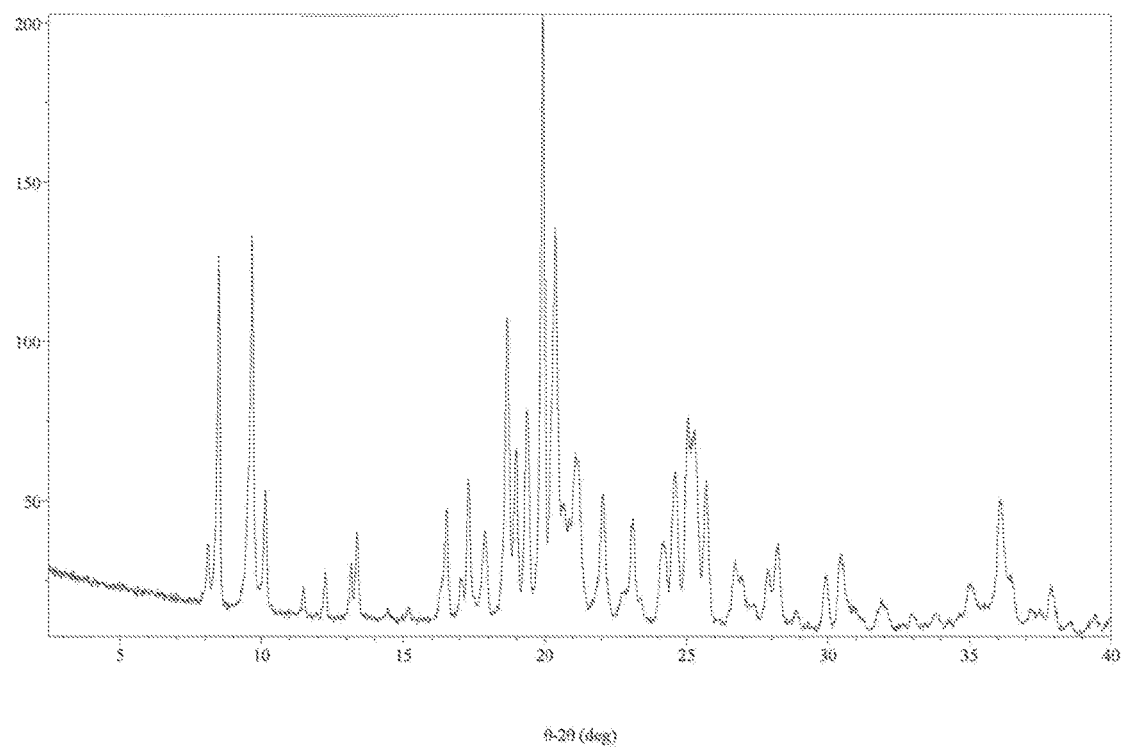
FIG. 1 is an XRD spectrum of a lyophilized cyclophosphamide composition according to an embodiment of the invention.

Various publications, articles and patents are cited or described in the background and throughout the specification; each of these references is herein incorporated by reference in its entirety. Discussion of documents, acts, materials, devices, articles or the like which has been included in the specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Unless otherwise stated, any numerical value, such as a concentration, a temperature, a period of time, or a range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Lyophilized Cyclophosphamide Composition

It was previously believed that the monohydrate form of cyclophosphamide was necessary for a stable product, but this assumption has been disproven in the present invention. It is surprisingly discovered in the present invention that a lyophilized cyclophosphamide solid composition containing anhydrous cyclophosphamide and mannitol is thermally stable over extended storage periods. The composition has a moisture content less than 2% by weight, preferably less than 1% by weight. The composition contains one or more crystalline forms that cannot be attributed to any of the known forms of cyclophosphamide or mannitol.

According to one embodiment of the invention, a lyophilized cyclophosphamide solid composition contains a mixture of cyclophosphamide anhydrous and mannitol polymorphs, including one or more novel crystalline forms exhibiting an X-ray powder diffraction (XRPD) spectrum having one or more peaks at diffraction angle (2θ) of 8.1±0.2°, 8.5±0.2°, 12.3±0.2° or 13.4±0.2°, preferably a 2θ of 8.5±0.2°. In one embodiment, the lyophilized cyclophosphamide solid composition contains one or more novel crystalline forms having a XRPD spectrum comprising peaks at 2θ of 8.1±0.2°, 8.5±0.2°, 12.3±0.2° and 13.4±0.2°. In a preferred embodiment of the invention, the lyophilized composition is substantially free of cyclophosphamide monohydrate.

More specifically, XRPD (X-ray Powder Diffraction), DVS (Dynamic Vapor Sorption) analysis, and HSM (hot stage microscopy) were performed to evaluate the crystallinity of compositions according to embodiments of the invention, and determine the components present in the compositions. It was found that compositions according to embodiments of the invention contain anhydrous cyclophosphamide and mannitol and more specifically contain anhydrous cyclophosphamide in racemate form and δ D-mannitol. Compositions according to embodiments of the present invention can further contain κ D-mannitol, β D-mannitol hemihydrate, and/or anhydrous cyclophosphamide in enantiopure form, depending on the particular sample. Surprisingly, the inventive compositions contain one or more crystalline forms that cannot be attributed to any of the known forms of cyclophosphamide or mannitol. The one or more novel crystalline forms exhibit an XRPD spectrum having one or more peaks at 2θ of 8.1±0.2°, 8.5±0.2°, 12.3±0.2° or 13.4±0.2°. Preferably, an inventive composition according to an embodiment of the present invention is substantially free of cyclophosphamide monohydrate, and no characteristic peaks corresponding to cyclophosphamide monohydrate is detected on the XRPD spectrum of the composition. The weight ratio of total cyclophosphamide to total mannitol in the composition is preferably 0.5 to 10, even more preferably 1.2 to 1.8, more preferably about 1.3.

Figure 2:
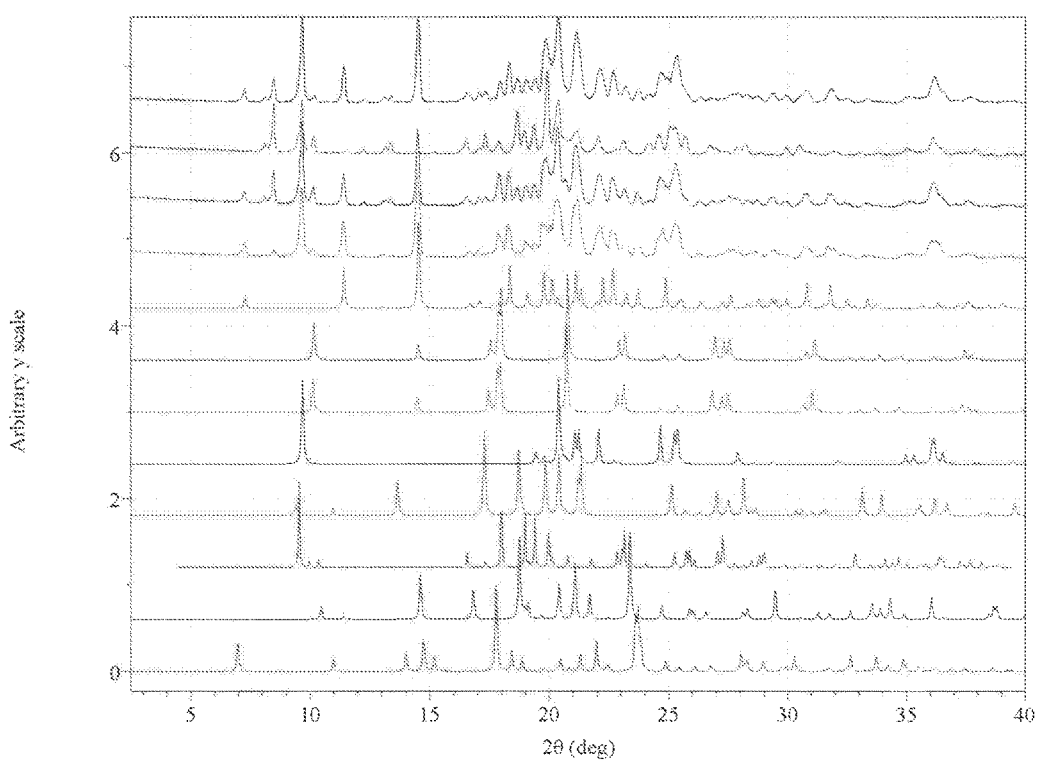
FIG. 2 is an XRPD pattern comparison of lyophilized cyclophosphamide compositions according to embodiments of the invention with known forms of cyclophosphamide and mannitol; the analyzed samples are, from top to bottom:
1. a lyophilized cyclophosphamide composition according to a first embodiment of the invention;
2. a lyophilized cyclophosphamide composition according to a second embodiment of the invention;
3. a lyophilized cyclophosphamide composition according to a third embodiment of the invention;
4. a lyophilized cyclophosphamide composition according to a fourth embodiment of the invention;
5. cyclophosphamide anhydrous racemate form (Cyclophosphamide racemate anhydrate, Jones, et al., *Acta Crystallogr., Sect. C*, vol. 52, p 2359, 1996);
6. S-cyclophosphamide P1 form (Adamiak et al., *J. Biosci.*, 32, 672, 1977);
7. cyclophosphamide anhydrous enantiopure form (Cyclophosphamide enantiopure: Karle et al., *J. Am. Chem. Soc.*, vol. 99, p 4803, 1977);
8. delta D-mannitol (Mannitol delta: Botez et al, *Powder Diffr.*, vol. 18, p 214, 2003);
9. kappa D-mannitol (The Crystal Structure of K Form of D-Mannitol, Kim et al., *Acta. Cryst.* B24, 1449-1455, 1968);
10. mannitol hemihydrate (Mannitol hemihydrate, Nunes et al., *J. Pharm. Sci.*, vol. 93, p 2800, 2004);
11. beta D-mannitol (Mannitol beta, Kaminsky et al., *Kristallogr.*, vol. 212, p 283, 1997); and
12. cyclophosphamide monohydrate (cyclophosphamide racemate monohydrate, Clardy et al., *Phosphorus*, vol. 4, p 151, 1974).

The characteristic peaks corresponding to components of a composition according to an embodiment of the invention can be seen in the representative XRD spectrum in FIG. 1. As shown in FIG. 2, no peak which corresponds to cyclophosphamide monohydrate is detected in the compositions according to embodiments of the present invention.

When a composition contains cyclophosphamide monohydrate, if the water content is not correctly controlled, there is a potential for excess water that would begin to degrade the cyclophosphamide during storage. Accordingly, inventive lyophilized cyclophosphamide solid compositions according to embodiments of the invention, which are substantially free of water or cyclophosphamide monohydrate, are advantageous because there is no potential for this degradation during storage. The inventive compositions have been shown to exhibit long term stability for longer than 3 months when stored at 5° C. or at 25° C./60% RH (relative humidity).

Lyophilization Process

The solid cyclophosphamide composition of the invention can be obtained by an inventive lyophilization process. Different from the prior art, the lyophilization processes according to embodiments of the invention do not require a rehydration step or an organic solvent. It comprises:

(1) preparing a solution containing cyclophosphamide, mannitol, and water;
(2) filling a receptacle with the solution;
(3) inserting the receptacle filled with the solution into a lyophilizer having a first shelf temperature of 0° C. to 25° C., preferably 3° C. to 8° C., and maintaining the first shelf temperature to allow all the solution to equilibrate at the first shelf temperature;
(4) cooling the lyophilizer to a second shelf temperature of −75 to −30° C., preferably −55° C. to −40° C., at a first controlled rate, and maintaining the second shelf temperature to allow the solution to form ice and to allow the temperature of the ice to reach a steady state;
(5) chilling condenser of the lyophilizer to a temperature below −40° C., preferably −50° C. or below;
(6) evacuating chamber of the lyophilizer to a pressure of less than 4500 μm Hg, preferably 150-250 μm Hg, and controlling the chamber pressure at the pressure of less than 4500 μm Hg, preferably 150-250 μm Hg, by bleeding in an inert gas;
(7) warming the lyophilizer to a third shelf temperature of −30 to 40° C., preferably 5° C. to 15° C., at a second controlled rate, and maintaining third shelf temperature and the chamber pressure at the pressure of less than 4500 μm Hg, preferably 150-250 μm Hg, to allow sublimation of the ice to thereby produce a sublimed composition; and
(8) setting the lyophilizer to a fourth shelf temperature of 0° C. to 40° C., preferably 15° C. to 25° C., and maintaining the fourth shelf temperature and the chamber pressure at the pressure of less than 4500 μm Hg to desorb remaining moisture to thereby produce the lyophilized cyclophosphamide solid composition.

Solution Preparation

According to an embodiment of the invention, a solution consisting essentially of cyclophosphamide monohydrate, mannitol, and water is prepared. That is, no additional solvents are contained in the solution. The solution can be prepared by known methods with cyclophosphamide anhydrous or cyclophosphamide monohydrate. Different form of mannitol (powder or solution) can be employed.

It has been found in the invention that significant degradation of cyclophosphamide can occur when the bulk solution temperature is maintained at 5° C. to 15° C., such as 12° C.±3° C., for an extended period of time. Therefore, it is preferable to achieve rapid dissolution of cyclophosphamide to leave sufficient time for filtrating, filling, and loading of the solution into the lyophilizer before the significant degradation occurs.

In a preferred embodiment of the invention, a rapid dissolution is achieved when mannitol powder is first added to water to form an aqueous solution, followed by chilling the solution to 5° C. to 15° C., more preferably 12° C.±3° C., and then adding the cyclophosphamide monohydrate (USP grade) to the chilled mannitol solution. The concentration of mannitol in the solution is preferably 14 mg/ml to 19.6 mg/ml. The concentration of cyclophosphamide monohydrate in the solution is preferably 20 to 28 mg/mL, and is more preferably kept at or below 25 mg/mL (equivalent to 23.4 mg/mL cyclophosphamide anhydrous). Such concentrations have been found to eliminate or minimize precipitation of the product from the solution, allowing for a clear, homogeneous solution when both solutes have been added.

The cyclophosphamide solution contains cyclophosphamide (anhydrous) and mannitol in specified ratios and amounts. For example, the solution can contain cyclophosphamide anhydrous and mannitol at a weight ratio of 0.5 to 10, more preferably 0.5 to 5, even more preferably 1.2 to 1.5, most preferably 1.3. Such concentrations can be employed to produce vials having different strengths. For example, a vial containing 500 mg cyclophosphamide (534.5 mg cyclophosphamide monohydrate) contains 375 mg mannitol, a vial containing 1 g cyclophosphamide (1069.0 mg cyclophosphamide monohydrate) contains 750 mg mannitol, and a vial containing 2 g cyclophosphamide (2138.0 mg cyclophosphamide monohydrate) contains 1500 mg mannitol.

In a preferred embodiment of the invention, a rapid dissolution is achieved by using cyclophosphamide monohydrate having a preferred particle size. The particle size can be characterized by the median diameter of particles of cyclophosphamide monohydrate used to prepare the solution. As used herein, the "d(0.5)" particle size distribution is the median diameter of the particle size distribution, and represents the particle size at which 50% of the particles are larger and 50% of the particles are smaller than the d(0.5) value. Similarly, the "d(0.1)" value is the particle size at which 10% of the particles are smaller and 90% of the particles are larger, and the "d(0.9)" value is the particle size at which 90% of the particles are smaller and 10% of the particles are larger. The particle size can be measured using methods known in the art, for example, as determined in dry-dispersion mode using a Malvern Mastersizer 2000 equipped with a Scirocco 2000 module (measuring range 0.02 to 2000 μm).

Preferably, the cyclophosphamide monohydrate used for the preparation of the solution for lyophilization has a d(0.5) particle size distribution of 300-800 μm, preferably 100-400 μm, for the preparation of the solution for lyophilization. The particle size of the cyclophosphamide monohydrate can be further characterized as having a d(0.1) particle size distribution of 40-180 μm, and/or as having a d(0.9) particle size distribution of about 300-800 μm.

In another preferred embodiment of the invention, a rapid dissolution is achieved by rapid mixing with a strong vortex, such as with a stir bar and/or overhead stirrer. The temperature is preferably maintained at 5° C. to 15° C., more preferably at 12° C.±3° C., during the stirring. However, as noted above, other methods of preparing the cyclophosphamide solution are also within the scope of the invention.

After the solution of mannitol and cyclophosphamide has been mixed, it is preferably filtered. In an exemplary embodiment, filtration is performed through a 0.2 μm sterilizing filter with a polyvinylidene fluoride (PVDF) membrane, such as a Millipak 20 filter. Filtration is performed to sterilize the bulk solution prior to performing an aseptic filling operation. This method of filtration is exemplary, not limiting, and other filtering methods and procedures which are known in the art would also be equally applicable for the method of the invention. The solution is kept chilled at 5° C. to 15° C., more preferably at 12° C.±3° C., in the starting and receiving vessels during filtration.

The components of the solution, cyclophosphamide monohydrate and mannitol which meet USP requirements, are commercially available. Cyclophosphamide monohydrate is preferably stored at −2° C. to −8° C. prior to use.

Receptacle Preparation

According to an embodiment of the invention, the lyophilization process involves filling the desired receptacle, container or vessel with a cyclophosphamide solution. The filling is performed at 5° C. to 15° C., such as at 12° C.±3° C.

Different receptacles can be utilized, such as molded vials or tubing. For the purposes of this description, the terms "container," "vial," and "receptacle" will be used interchangeably. A variety of vial sizes can be utilized, including, without limitation, 20 mL, 50 mL, and 100 mL molded vials.

Each vial is filled with cyclophosphamide to a desired target quantity of cyclophosphamide depending on the concentration in the solution, such as 10 mL for a 20 mL vial, 20 mL for a 50 mL vial, or 80 mL for a 100 mL vial. Methods of filling the vials or receptacles are known in the art and can be used in the invention in view of the present disclosure.

Chamber Filling and Pressurization

According to an embodiment of the invention, the lyophilization process involves inserting the vial(s) into a lyophilizer chamber having shelves at a shelf temperature of 0° C. to 25° C., more preferably 3° C. to 8° C., even more preferably 5° C., for preventing nucleation (onset of freezing) and maintaining stability of cyclophosphamide in solution. Any lyophilizer can be utilized for the process of the invention, such as a Hull Model 8FS15C pilot size lyophilizer. The vial(s) are placed onto the shelves of the lyophilizer.

The chamber can be evacuated to greater than 10 psia, such as 12 psia, to ensure that the chamber is airtight.

Temperature Control

According to an embodiment of the invention, the lyophilization process involves maintaining the lyophilizer at the shelf temperature of 0° C. to 25° C., such as 3° C. to 8° C., or 5° C., and the pressure in the chamber at greater than 10 psia to equilibrate the temperature of the cyclophosphamide solution contained in the vials. The temperature of the shelves is controlled at a target set point of 0° C. to 25° C. until all of the product has been loaded onto the shelves. This temperature is then held for an appropriate time so that all of the product samples can equilibrate to the target temperature. Such a time period can be determined by routine experimentation in view of the present disclosure. For example, it can be 1 to 15 hours. It is desirable to equilibrate the product to the target temperature so that all samples (receptacles) will have the same thermal history prior to freezing.

Temperature Reduction and Maintenance

According to an embodiment of the invention, the lyophilizer shelves are chilled to a shelf temperature of −75° C. to −30° C. at an average controlled rate, such as 6° C. to 120° C. per hour, for example, but not limited to, 15, 20, 25 or 30° C. per hour, to ensure adequate solidification of the product, for example, by keeping the product below a minimum freezing temperature, such as −32° C. It has been found that slow cooling of the cyclophosphamide solution, and a moderate ramp speed leads to a more uniform freezing throughout the vial by ensuring a more uniform temperature distribution throughout the vial. In a preferred embodiment, the shelves are chilled at an average controlled rate of 30° C. per hour. Thus, the time required to cool the lyophilizer from the initial shelf temperature of 0° C. to 25° C. to the second shelf temperature of −75° C. to −30° C. can be one to four hours.

After cooling, the temperature of the lyophilizer shelves are maintained at −75° C. to −30° C. and the chamber is maintained at the pressure of greater than 10 psia, preferably at 11 to 13 psia, for additional time to equilibrate the temperature of the cyclophosphamide solution contained in the receptacles and produce frozen solutions (ice). The appropriate time required for equilibration and solidification can be determined by routine experimentation. For example, it can be 1 to 20 hours. The time is selected to ensure that there is sufficient time for the product temperature to reach a steady state prior to sublimation.

In one embodiment of the invention, an additional warming/cooling sequence for annealing is optionally performed after cooling to the shelf temperature of −75° C. to −30° C. and prior to chilling of the condenser. Specifically, the shelves are warmed to a shelf temperature of −30° C. to less than 0° C., preferably −20° C. to −10° C., at a controlled rate, such as an average rate of 15° C. per hour or 30° C. per hour, and then cooled back to the shelf temperature of −75° C. to −30° C. at a controlled rate, such as an average rate of 15° C. per hour or 30° C. per hour. This shelf temperature of −75° C. to −30° C. is then maintained to equilibrate the temperature of the cyclophosphamide solution and produce a frozen solution, such as for 1 to 15 hours, preferably 3 to 4 hours.

Chilling of the Condenser and Evacuating the Chamber

The condenser of the lyophilizer is cooled to below −40° C., such as −50° C. or below, to ensure that enough water vapor can be stripped out of the air in the chamber to prevent fouling of the vacuum pump. The lyophilizer chamber is then evacuated to a pressure of less than 4500 microns of mercury (μm Hg), preferably 150-250 μm. The chamber pressure is then controlled in this range by, such as, but not limited to, bleeding in an inert gas such as the preferred nitrogen. More preferably, 0.1 or 0.2 micron filtered nitrogen NF is utilized to control the chamber pressure at the desired level.

Sublimation

According to an embodiment of the invention, the ice in the frozen cyclophosphamide solution is sublimed preferably by the following steps.

The sublimation process involves controlled gradual warming of the lyophilization shelves for the sublimation of the cyclophosphamide solution. In a primary drying sequence, the shelves are warmed to −30° C. to 40° C., preferably 5° C. to 15° C. at a controlled rate, such as an average rate of 6° C. to 120° C. per hour, including, for example but not limited to 10, 15 or 20° C. per hour, and then maintained at −30° C. to 40° C., preferably 5° C. to 15° C. for a sufficient time, such as 30-190 hours, until all the ice has sublimed.

It has been found that holding the sample at a low temperature under vacuum for an extended time following sublimation results in a predominantly anhydrous compound. Thus, in a secondary drying sequence, the shelves are set to 0° C. to 40° C., preferably 0° C. to 10° C. or 15° C. to 25° C., at a controlled rate such as 30° C. per hour or slower, and maintained at this temperature for, e.g., 3 to 12 hours, to desorb remaining moisture. The time needed for the final step can be determined by routine experimentation in view of the present disclosure. Secondary drying thus allows remaining moisture to be removed from the product by desorption while maintaining the product at a temperature well below the melting temperature observed by DSC (differential scanning calorimetry).

Following sublimation, the resulting lyophilized cyclophosphamide product is a uniform, dense, white cake which, when reconstituted for use, forms a clear, colorless solution.

The process according to the invention is a robust process which results in a lyophilized product that is thermally stable and can be consistently manufactured. In contrast with lyophilized cyclophosphamide preparations produced by known processes, the product according to the invention includes one or more novel crystalline forms exhibiting an X-ray powder diffraction (XRPD) spectrum having one or more peaks at diffraction angle (2θ) of 8.1±0.2°, 8.5±0.2°, 12.3±0.2° or 13.4±0.2°. It has a moisture level less than 2% by weight, preferably 1% by weight or less, and yet is still thermally stable. In a preferred embodiment of the invention, the lyophilized composition contains only the anhydrous form of cyclophosphamide with no evidence of the crystalline monohydrate form.

The invention will now be described in connection with the following non limiting examples.

EXAMPLES

General Procedures

Cyclophosphamide monohydrate was obtained from AMPAC Fine Chemicals (Rancho Cordova, Calif.) and stored at 2° C. to 8° C. until use. Mannitol, USP, EP was obtained from Millipore, vials and tubing were obtained from SGD or Thuringer, and stoppers were obtained from West. A Hull Model 8FS15C pilot size lyophilizer was utilized for processing.

Cyclophosphamide solutions were formulated to contain mannitol, cyclophosphamide and water, and were filtered through a 0.2 μm sterilizing filter with a polyvinylidene fluoride membrane (Millipak 20 filter), then filled into washed vials (volume 20 to 100 ml) to a target fill quantity ranging from 200 mg/vial to 2000 mg/vial cyclophosphamide anhydrous. After loading the product, the lyophilizer was evacuated to 12 psia and the desired lyophilization cycle was performed. Data were recorded electronically every five minutes. Monitoring was performed in process using a Hastings Gauge (thermocouple vacuum gauge), which indicates the end of sublimation in primary drying or the end of desorption in secondary drying. Following lyophilization, products were physically inspected to evaluate the uniformity of appearance in color, texture, shape, and structure to assess the relative effects of processing. Solutions were reconstituted using purified water and evaluated to determine the presence or absence of insoluble material, clarity, color, and time required to fully dissolve the cyclophosphamide. Moisture testing was performed using coulometric Karl Fischer Titration, glass transition and/or melting point of solid materials was determined from high temperature differential scanning calorimetry (HT-DSC), and residual moisture determination was performed using thermogravimetric analysis (TGA).

Example 1: Investigation of Cyclophosphamide Dissolution

A series of experiments were performed in order to evaluate the effects of order of addition, mixing method and speed, and impact of cyclophosphamide monohydrate particle size distribution on the dissolution of cyclophosphamide. Various compounding methods were investigated in order to achieve rapid dissolution within one hour in order to leave sufficient time for filtration, filtering, and loading of the lyophilizer within twelve hours. The data obtained from these studies are found in Tables 1-3 below:

TABLE 1

| | Bulk Solution Concentrations | | | |
|---|---|---|---|---|
| Study | Cyclophosphamide Monohydrate (mg/mL) | Cyclophosphamide (mg/mL) | Mannitol, USP, EP (mg/mL) | Complete Dissolution within time limit? (yes/no) |
| A | 21.4 | 20.0 | 15.0 | yes |
| B | 29.9 | 28.0 | 21.0 | no |
| C | 29.9 | 28.0 | 21.0 | no |

TABLE 1-continued

Bulk Solution Concentrations

| Study | Cyclophosphamide Monohydrate (mg/mL) | Cyclophosphamide (mg/mL) | Mannitol, USP, EP (mg/mL) | Complete Dissolution within time limit? (yes/no) |
|---|---|---|---|---|
| D | 26.7 | 25.0 | 19.0 | no |
| E | 29.9 | 28.0 | 21.0 | no |
| F | 21.4 | 20.0 | 15.0 | no |
| G | 29.9 | 28.0 | 21.0 | yes |
| H | 28.0 | 26.2 | 21.0 | no |
| I | 25.0 | 23.4 | 18.8 | no |
| J | 25.0 | 23.4 | 18.8 | no |
| K | 28.0 | 26.2 | 21.0 | no |
| L | 25.0 | 23.4 | 18.8 | yes |
| M | 25.0 | 23.4 | 17.63 | yes |

TABLE 2

Order of Addition

| Rx | Order of Addition (Concentration) | | |
|---|---|---|---|
| | 1st | 2nd | 3rd |
| 1 | Mannitol | Chill | Cyclophosphamide |
| 2 | Chill | Cyclophosphamide | Mannitol |
| 3 | Chill | Cyclophosphamide | Mannitol, added as a solution |
| 4 | Mannitol | Cyclophosphamide | Chill |

TABLE 3

Bulk Solution Properties

| Study | Cyclophosphamide Anhydrous Concentration (mg/mL) | Dissolution (minutes) | Order of Addition (see Table 2) | Mixing Method |
|---|---|---|---|---|
| A | 20.0 | 105 | Rx1 | Stir Bar |
| B | 28.0 | 165 | Rx1 | Stir Bar |
| C | 28.0 | 54 | Rx1 | Stir Bar |
| D | 28.0 | 59 | Rx2 | Stir Bar |
| E | 28.0 | 160 | Rx3 | Stir Bar |
| F | 28.0 | 21 | Rx4 | Stir Bar |
| G | 28.0 | 190 | Rx1 | Stir Bar |
| H | 25.0 | 69 | Rx1 | Stir Bar |
| I | 28.0 | 267 | Rx1 | Stir Bar and overhead |
| J | 20.0 | 63 | Rx1 | Stir Bar |
| K | 28.0 | 98 | Rx2 | Stir Bar |
| L | 26.2 | 170 | Rx1 | Stir Bar |
| M | 26.2 | 111 | Rx1 | Overhead |
| N | 26.2 | 151 | Rx1 | Overhead |
| O | 23.4 | 60 | Rx1 | Overhead |
| P | 23.4 | 108 | Rx2 | Overhead |
| Q | 26.2 | 129 | Rx2 | Overhead |
| R | 23.4 | 90 | Rx1 | Overhead |
| S | 23.4 | 35 | Rx1 | Overhead |
| T | 23.4 | 40 | Rx1 | Overhead |

From these studies, it was determined that the preferred dissolution method (Rx1 in Table 2) involves first adding mannitol powder to water to form an aqueous solution, followed by chilling the solution and then adding the cyclophosphamide monohydrate to the chilled mannitol solution. The concentration of cyclophosphamide monohydrate is preferably 25.0 mg/ml or lower, and particle size is also preferably controlled. Table 3b lists the particle size distributions of some batches of cyclophosphamide monohydrate used in the preparation of the solution, wherein the particle size distribution was measured using a Malvern particle size analyzer. In addition, rapid mixing with a strong vortex is also preferred to achieve rapid dissolution.

TABLE 3b

Particle size distribution of cyclophosphamide monohydrate

| Batch No. | Particle Size Distribution (μm) | | |
|---|---|---|---|
| | d (0.1) | d (0.5) | d (0.9) |
| 1 | 75 | 261 | 653 |
| 2 | 166 | 317 | 547 |
| 3 | 175 | 362 | 667 |
| 4 | 65 | 256 | 781 |
| 5 | 48 | 131 | 331 |

Example 2: Investigation of Filling and Lyophilization of Cyclophosphamide: 2000 mg Presentations 2000 mg/vial presentations of cyclophosphamide were prepared having, e.g., 25 mg/ml cyclophosphamide monohydrate (equivalent to 23.5 mg/ml cyclophosphamide), 17.6 mg/ml mannitol, and water. A bulk cyclophosphamide solution was prepared at a temperature 10° C. with a dissolution time of about 68 minutes. The solutions were filled into vials, loaded onto the shelves of a lyophilizer at 5° C., and the chamber was evacuated to within 11-13 psia after loading. Tables 4a, 4b, 5a and 5b list freeze drying parameters of exemplary processes for lyophilization of 2000 mg/vial presentations.

TABLE 4a

Summary of Target Lyophilization Cycle Parameters: (2000 mg)

| Step | Shelf Temp. Setpoint (° C.) | Soak Time (hours) | Ramping Rate (° C./hour) | Pressure Setpoint |
|---|---|---|---|---|
| Product Loading | 5 | 4.0 | | Evac. to 12 PSIA to ensure chamber is airtight |
| | | | 30.0 | |
| Freezing | −50 | 6.0 | | |
| | | | 15.0 | |
| Primary Drying | 10 | 182.0 | | 200 microns of Hg |
| | | | 30.0 | |
| Secondary Drying | 20 | 10.0 | | |
| Stoppering | 20 | — | | 10.0 PSIA |

TABLE 4b

Summary of Target Lyophilization Cycle Parameters: (2000 mg)

| Step | Shelf Temp. Setpoint (° C.) | Soak Time (hours) | Ramping Rate (° C./hour) | Pressure Setpoint |
|---|---|---|---|---|
| Product Loading | 6 | 4.0 | | Evac. To 12 PSIA to ensure chamber is airtight |
| | | | 30.0 | |
| Freezing | −52 | 6.0 | | |
| | | | 15.0 | |
| Primary Drying | 10 | 175.0 | | 200 microns of Hg |
| | | | 30.0 | |
| Secondary Drying | 5 | 17 | | |
| Stoppering | 5 | — | | 10.0 PSIA |

TABLE 5a

Summary of Target Lyophilization Cycle Parameters: (2000 mg)

| Step | Shelf Temp. Setpoint (° C.) | Soak Time (hours) | Ramping Rate (° C./hour) | Pressure Setpoint |
|---|---|---|---|---|
| Product Loading | 5 | 4.0 |  | Evac. To 12 PSIA to ensure chamber is airtight |
| Freezing | −50 | 6.0 | 30.0 |  |
| Primary Drying | 12 | 160.0 | 15.0 | 200 microns of Hg |
| Secondary Drying | 20 | 4.0 | 30.0 |  |
| Stoppering | 20 | — |  | 10.0 PSIA |

TABLE 5b

Summary of Target Lyophilization Cycle Parameters: (2000 mg)

| Step | Shelf Temp. Setpoint (° C.) | Soak Time (hours) | Ramping Rate (° C./hour) | Pressure Setpoint |
|---|---|---|---|---|
| Product Loading | 5 | 4.0 |  | Evac. To 12 PSIA to ensure chamber is airtight |
| Freezing | −50 | 3.5 | 30.0 |  |
| Annealing | −20 | 4.0 | 15.0 |  |
| Freezing | −50 | 4.0 | 30.0 |  |
| Drying | 5 | 8.0 | 15.0 | 150 microns of Hg |
|  | 10 | 3.0 |  |  |
|  | 15 | 3.0 |  |  |
|  | 5 | 4.0 |  |  |
|  | 5 | 2.1 |  | 200 microns |
|  | 5 | 163.0 |  | 250 microns |
| Stoppering | 5 | — |  | 10.0 PSIA |

Physical appearance for the product vials showed a uniform, dense, white cake with no side shrinkage. Reconstitution was performed with Purified Water, USP. The reconstituted samples resulted in clear, colorless solutions. The pH dropped from 4.8 to 3.5-3.6 post-lyophilization.

Example 3: Investigation of Filling and Lyophilization of Cyclophosphamide: 500 mg Presentations 500 mg/vial presentations of cyclophosphamide were prepared having, e.g., 25 mg/ml cyclophosphamide monohydrate (equivalent to 23.4 mg/ml cyclophosphamide), 17.5 mg/ml mannitol, and water. A bulk cyclophosphamide solution was prepared at a temperature 10-11° C. with a dissolution time of about 45 minutes. The bulk solutions were filled and loaded onto the shelves of a lyophilizer at 5° C., and the chamber was evacuated to within 11-13 psia after loading. Tables 6a, 6b, 7a and 7b list freeze drying parameters of exemplary processes for lyophilization of 500 mg/vial presentations.

TABLE 6a

Summary of Target Lyophilization Cycle Parameters: (500 mg)

| Step | Shelf Temp. Setpoint (° C.) | Soak Time (hours) | Ramping Rate (° C./hour) | Pressure Setpoint |
|---|---|---|---|---|
| Product Loading | 5 | 3.0 |  | Evac. To 12 PSIA to ensure chamber is airtight |
| Freezing | −50 | 4.0 | 30.0 |  |
| Primary Drying | 10 | 50.0 | 15.0 | 200 microns of Hg |
| Secondary Drying | 20 | 8.5 | 30.0 |  |
| Stoppering | 20 | — |  | 10.0 PSIA |

TABLE 6b

Summary of Target Lyophilization Cycle Parameters: (500 mg)

| Step | Shelf Temp. Setpoint (° C.) | Soak Time (hours) | Ramping Rate (° C./hour) | Pressure Setpoint |
|---|---|---|---|---|
| Product Loading | 5 | 3.0 |  | Evac. To 12 PSIA to ensure chamber is airtight |
| Freezing | −50 | 4.0 | 30.0 |  |
| Primary Drying | 12 | 40.0 | 15.0 | 200 microns of Hg |
| Secondary Drying | 5 | 10 | 30.0 |  |
| Stoppering | 5 | — |  | 10.0 PSIA |

TABLE 7a

Summary of Target Lyophilization Cycle Parameters: (500 mg)

| Step | Shelf Temp. Setpoint (° C.) | Soak Time (hours) | Ramping Rate (° C./hour) | Pressure Setpoint |
|---|---|---|---|---|
| Product Loading | 5 | 3.0 |  | Evac. To 12 PSIA to ensure chamber is airtight |
| Freezing | −50 | 2.5 | 30.0 |  |
| Annealing | −20 | 4.0 | 15.0 |  |
| Freezing | −50 | 3.0 | 30.0 |  |
| Drying | 5 | 2.0 | 15.0 | 150 microns |
|  | 5 | 2.0 |  | 200 microns |
|  | 5 | 4.0 |  | 250 microns |
|  | 10 | 3.0 |  |  |
|  | 15 | 3.0 |  |  |
|  | 5 | 53.7 |  |  |
| Stoppering | 5 |  |  | 10.0 PSIA |

TABLE 7b

Summary of Target Lyophilization Cycle Parameters: (500 mg)

| Step | Shelf Temp. Setpoint (° C.) | Soak Time (hours) | Ramping Rate (° C./hour) | Pressure Setpoint |
|---|---|---|---|---|
| Product Loading | 5 | 3.5 |  | Evac. To 12 PSIA to ensure chamber is airtight |
| Freezing | −50 | 5.0 | 30.0 |  |
| Drying | 5 | 4.0 | 15.0 | 150 microns |
|  | 5 | 4.0 |  | 250 microns |
|  | 10 | 3.0 |  |  |

TABLE 7b-continued

Summary of Target Lyophilization Cycle Parameters: (500 mg)

| Step | Shelf Temp. Setpoint (° C.) | Soak Time (hours) | Ramping Rate (° C./hour) | Pressure Setpoint |
|---|---|---|---|---|
|  | 15 | 3.0 |  |  |
|  | 5 | 62.0 |  |  |
| Stoppering | 5 | — |  | 10.0 PSIA |

Physical appearance for the product vials showed a uniform, dense, white cake with no side shrinkage. Reconstitution was performed with Purified Water, USP. The reconstituted samples resulted in clear, colorless solutions. The pH dropped from 4.1 to 3.9 post-lyophilization. Karl Fisher results showed an average moisture level of less than 1% (w/w), such as 0.34% (w/w).

Example 4: Investigation of Filling and Lyophilization of Cyclophosphamide: 200 mg Presentations 200 mg/vial presentations of cyclophosphamide was prepared having, e.g., 25 mg/ml cyclophosphamide monohydrate (equivalent to 23.4 mg/ml cyclophosphamide), 17.5 mg/ml mannitol, and water. A bulk cyclophosphamide solution was prepared at a temperature 10-14° C. with a dissolution time of about 38 minutes. The bulk solutions were filled into vials, loaded onto the shelves of a lyophilizer at 5° C., and the chamber was evacuated to within 11-13 psia after loading. Tables 8a, 8b, 9a and 9b list freeze drying parameters of exemplary processes for lyophilization of 200 mg/vial presentations.

TABLE 8a

Summary of Target Lyophilization Cycle Parameters: (200 mg)

| Step | Shelf Temp. Setpoint (° C.) | Soak Time (hours) | Ramping Rate (° C./hour) | Pressure Setpoint |
|---|---|---|---|---|
| Product Loading | 5 | 2.5 |  | Evac. To 12 PSIA to ensure chamber is airtight |
|  |  |  | 30.0 |  |
| Freezing | −50 | 3.0 |  |  |
|  |  |  | 15.0 |  |
| Primary Drying | 10 | 32.0 |  | 200 microns of Hg |
|  |  |  | 30.0 |  |
| Secondary Drying | 20 | 4.0 |  |  |
| Stoppering | 20 | — |  | 10.0 PSIA |

TABLE 8b

Summary of Target Lyophilization Cycle Parameters: (200 mg)

| Step | Shelf Temp. Setpoint (° C.) | Soak Time (hours) | Ramping Rate (° C./hour) | Pressure Setpoint |
|---|---|---|---|---|
| Product Loading | 5 | 2.5 |  | Evac. To 12 PSIA toensure chamber is airtight |
|  |  |  | 30.0 |  |
| Freezing | −50 | 3.0 |  |  |
|  |  |  | 15.0 |  |
| Primary Drying | 12 | 27.0 |  | 200 microns of Hg |
|  |  |  | 30.0 |  |
| Secondary Drying | 5 | 2 |  |  |
| Stoppering | 5 | — |  | 10.0 PSIA |

TABLE 9a

Summary of Target Lyophilization Cycle Parameters: (200 mg)

| Step | Shelf Temp. Setpoint (° C.) | Soak Time (hours) | Ramping Rate (° C./hour) | Pressure Setpoint |
|---|---|---|---|---|
| Product Loading | 6 | 3 |  | Evac. To 12 PSIA to ensure chamber is airtight |
|  |  |  | 30.0 |  |
| Freezing | −55 | 2.0 |  |  |
|  |  |  | 15.0 |  |
| Primary Drying | 8 | 32.0 |  | 200 microns of Hg |
|  |  |  | 30.0 |  |
| Secondary Drying | 5 | 4.0 |  |  |
| Stoppering | 5 | — |  | 10.0 PSIA |

TABLE 9b

Summary of Target Lyophilization Cycle Parameters: (200 mg)

| Step | Shelf Temp. Setpoint (° C.) | Soak Time (hours) | Ramping Rate (° C./hour) | Pressure Setpoint |
|---|---|---|---|---|
| Product Loading | 5 | 2.5 |  | Evac. To 12 PSIA to ensure chamber is airtight |
|  |  |  | 30.0 |  |
| Freezing | −50 | 3.0 |  |  |
|  |  |  | 15.0 |  |
| Drying | 5 | 2.5 |  | 150 microns |
|  | 5 | 2.5 |  | 250 microns |
|  | 10 | 2.0 |  |  |
|  | 15 | 2.0 |  |  |
|  | 5 | 30.0 |  |  |
| Stoppering | 5 | — |  | 10.0 PSIA |

Physical appearance for the product vials showed a uniform, dense, white cake with no side shrinkage. Reconstitution was performed with Purified Water, USP. The reconstituted samples resulted in clear, colorless solutions. The pH dropped from 4.8 to 3.9-4.0 post-lyophilization. The average residual moisture is less than 1% (w/w), such as about 0.36% (w/w).

Example 5: Physical Characterization of Lyophilized Cyclophosphamide Compositions Several samples of lyophilized cyclophosphamide were analyzed using XRPD (X-ray Powder Diffraction), DVS (Dynamic Vapor Sorption) analysis, and HSM (hot stage microscopy) to evaluate the crystallinity and determine the components present in the samples. An XRPD spectrum from one representative sample is shown in FIG. 1.

FIG. 2 shows the XRPD pattern comparison of four lyophilized cyclophosphamide compositions according to embodiments of the invention (the top four spectra) with known forms of non-GMP cyclophosphamide and mannitol. It was determined that the lyophilized cyclophosphamide compositions according to embodiments of the invention all contain an unidentified peak at 8.5° (2θ), and additionally one or more peaks at 8.1°, 12.3° and 13.4° (2θ), representing one or more novel crystal forms that cannot be attributed to any of the known forms of cyclophosphamide or mannitol. The compositions contained anhydrous cyclophosphamide and mannitol, more specifically cyclophosphamide anhydrous enantiopure form and δ D-mannitol. Additionally, depending on the particular process steps used for preparation, the compositions further contained κ D-mannitol, β D-mannitol hemihydrate, and/or cyclophosphamide anhydrous racemate form in varying ratios. However, the compositions were substantially free of cyclophosphamide monohydrate.

It will be appreciated by those skilled in the art that changes could be made to the embodiment described above without departing from the broad inventive concepts thereof. Also, based on this disclosure, a person of ordinary skill in the art would further recognize that the relative proportions of the components illustrated could be varied without departing from the spirit and scope of the invention. It is understood, therefore, that this invention is not limited to the particular embodiment disclosed, but it is intended to cover modifications within the spirit and scope of the present invention as defined by the appended claims.

We claim:

1. A lyophilized cyclophosphamide solid composition comprising cyclophosphamide and mannitol, wherein the composition contains one or more crystalline forms exhibiting an X-ray powder diffraction (XRPD) spectrum having a peak at diffraction angle (2θ) of 8.5±0.2, and the composition has a moisture content of less than 2% by weight.

2. The lyophilized cyclophosphamide solid composition of claim 1 having a moisture content of less than 1% by weight.

3. The lyophilized cyclophosphamide solid composition of claim 1, wherein there is no evidence of cyclophosphamide monohydrate in the XRPD spectrum.

4. The lyophilized cyclophosphamide solid composition of claim 1, containing cyclophosphamide anhydrous enantiopure form and δ D-mannitol.

5. A lyophilized cyclophosphamide solid composition consisting essentially of cyclophosphamide and mannitol, wherein the composition contains one or more crystalline forms having an X-ray powder diffraction (XRPD) spectrum comprising a peak at diffraction angle (2θ) of 8.5±0.2°, and the composition has a moisture content of less than 2% by weight.

6. The lyophilized cyclophosphamide solid composition of claim 5, wherein there is no evidence of cyclophosphamide monohydrate in the XRPD spectrum.

7. The lyophilized cyclophosphamide solid composition of claim 6, having a weight ratio of mannitol to cyclophoshamide anhydrous of 1.2 to 1.8.

8. The lyophilized cyclophosphamide solid composition of claim 1, wherein the XRPD spectrum further comprises peaks at diffraction angle (2θ) of 8.1±0.2°, 12.3±0.2°, and 13.4±0.2°.

9. The lyophilized cyclophosphamide solid composition of claim 5 having a moisture content of less than 1% by weight.

* * * * *